(12) United States Patent
Acharya et al.

(10) Patent No.: US 6,298,112 B1
(45) Date of Patent: Oct. 2, 2001

(54) METHODS AND APPARATUS FOR HELICAL MULTI-FRAME IMAGE RECONSTRUCTION IN A COMPUTED TOMOGRAPHY FLUORO SYSTEM INCLUDING DATA COMMUNICATIONS OVER A NETWORK

(75) Inventors: Kishore Acharya, Brookfield; Sandeep Dutta, New Berlin; Jiang Hsieh, Waukesha, all of WI (US)

(73) Assignee: GE Medical Systems Global Technology Co. LLC, Waukesha, WI (US)

( * ) Notice: Subject to any disclaimer, the term of this patent is extended or adjusted under 35 U.S.C. 154(b) by 0 days.

(21) Appl. No.: 09/472,530

(22) Filed: Dec. 27, 1999

Related U.S. Application Data

(63) Continuation-in-part of application No. 09/108,676, filed on Jul. 1, 1998, now Pat. No. 6,038,278.

(51) Int. Cl.⁷ ........................................................ A61B 6/03
(52) U.S. Cl. ................................. 378/15; 378/4; 378/901
(58) Field of Search .................................. 378/4, 15, 901

(56) References Cited

U.S. PATENT DOCUMENTS

| 4,736,399 | 4/1988 | Okazaki | 378/99 |
| 5,412,563 | 5/1995 | Cline et al. | 364/413.22 |
| 6,101,407 | * 8/2000 | Groezinger | 600/407 |
| 6,198,283 | * 3/2001 | Foo et al. | 324/309 |

\* cited by examiner

Primary Examiner—David V. Bruce
(74) Attorney, Agent, or Firm—Foley & Lardner; Christian G. Cabou

(57) ABSTRACT

A method for producing a base tomographic image and a subsequent tomographic image of an object using projection data acquired in a scan with a system which includes an x-ray source and a detector array which includes a plurality of detectors. The method includes applying a segmentation algorithm to the projection data to generate base image data comprising a plurality of segments; generating image data for each segment; generate subsequent image data based on image data of each segment; and communicating image data, segments, subsequent image data, or base image data to a remote facility via a network. The remote facility provides remote services.

17 Claims, 6 Drawing Sheets

METHODS AND APPARATUS FOR HELICAL MULTI-FRAME IMAGE RECONSTRUCTION IN A COMPUTED TOMOGRAPHY FLUORO SYSTEM INCLUDING DATA COMMUNICATIONS OVER A NETWORK

CROSS-REFERENCE TO RELATED APPLICATIONS

This application is a continuation-in-part (CIP) of U.S. patent application Ser. No. 09/108,676, entitled "Methods And Apparatus For Helical Multi-Frame Image Reconstruction In A Computed Tomography Fluoro System" by Kishore Achar a et al. filed on Jul. 1, 1998 now U.S. Pat. No. 6,038,278.

BACKGROUND OF THE INVENTION

The present invention relates generally to the field of medical diagnostic systems, such as imaging systems. More particularly, the invention relates to an apparatus and technique for multi-frame image reconstruction in a CT fluoroscopic system.

In at least one known CT system configuration, an x-ray source projects a fan-shaped beam which is collimated to lie within an X-Y plane of a Cartesian coordinate system and generally referred to as the "imaging plane". The x-ray beam passes through the object being imaged, such as a patient. The beam, after being attenuated by the object, impinges upon an array of radiation detectors. The intensity of the attenuated beam radiation received at the detector array is dependent upon the attenuation of the x-ray beam by the object. Each detector element of the array produces a separate electrical signal that is a measurement of the beam attenuation at the detector location. The attenuation measurements from all the detectors are acquired separately to produce an attenuation profile.

In known third generation CT systems, the x-ray source and the detector array are rotated with a gantry within the imaging plane and around the object to be imaged so that the angle at which the x-ray beam intersects the object constantly changes. A group of x-ray attenuation measurements, i.e., projection data, from the detector array at one gantry angle is referred to as a "view". A "scan" of the object comprises a set of views made at different gantry angles, or view angles, during one revolution of the x-ray source and detector. In an axial scan, the projection data is processed to construct an image that corresponds to a two dimensional slice taken through the object. One method for reconstructing an image from a set of projection data is referred to in the art as the filtered back projection technique. This process converts the attenuation measurements from a scan into integers called "CT numbers" or "Hounsfield units", which are used to control the brightness of a corresponding pixel on a cathode ray tube display.

Certain reconstruction process steps are known to produce noise structures in an image. For example, during a "cine" scan, i.e., a scan in which the patient remains stationary while the data for the prescribed number of slices is acquired, underscan weighting ("USW") is employed to reduce motion artifacts that result when patient anatomy moves during the scan. Underscan weighting algorithms typically weight the collected data as a function of view angle and detector channel index. Specifically, prior to filtered back projection, the data is weighted according to a underscan weighting factor, which is a function of both the view angle and detector angle. Particularly, projection data is first filtered, then weighted, and subsequently back-projected to generate each image.

To reduce the total scan time, a "helical" scan may be performed. To perform a "helical" scan, the patient is moved while the data for the prescribed number of slices is acquired. Such a system generates a single helix from a one fan beam helical scan. The helix mapped out by the fan beam yields projection data from which images in each prescribed slice may be reconstructed.

Reconstruction algorithms for helical scanning typically use helical weighting ("HW") algorithms which weight the collected data as a function of view angle and detector channel index. Specifically, prior to filtered back projection, the data is weighted according to a helical weighting factor, which is a function of both the view angle and detector angle. As with underscan weighting, in a HW algorithm, projection data is filtered, weighted, and backprojected to generate each image.

In a cine scan context and a helical scan context, the same projection data is repeatedly filtered, weighted, and back-projected even though it is continually assigned the same weight. For example, projection data $P_1$ may be weighted $w_1$ to generate a first image $I_1$, and also weighted $w_2$ to generate a second image $I_2$. However, second image $I_2$ cannot be generated without re-filtering, re-weighting and re-backprojecting projection data $P_1$. The underscan weighting algorithms and the helical weighting algorithms both require each image $I_1$ and $I_2$ to be independently generated from projection data $P_1$. Therefore, significant computational redundancy occurs with both helical weighting algorithms and underscan weighting algorithms.

Reconstruction techniques for improving certain aspects of image generation are known. For example, overscan weighting is employed to decrease computational redundancy associated with reconstructing overlapping images with projection data. Particularly, in overscan weighting, the collected projection data is weighted only as a function of view angle. Therefore, while not completely eliminating computational redundancy, overscan weighting reduces the computations necessary for image reconstruction. Moreover, overscan weighting is known to reduce motion artifacts that result when patient anatomy moves during a 360 degree CT scan. Patient motion causes views at the beginning and ending projections to be inconsistent and discontinuous. However, while overscan weighting is successful in reducing some motion artifacts, overscan weighting is not as effective as, for example, other helical weighting algorithms. Therefore, the overscan weighting is often precluded during helical scans.

In CT fluoroscopic systems ("CT Fluoro"), it is known to generate sequential frames of images. A frame, like a view, corresponds to a two dimensional slice taken through the imaged object. Particularly, projection data is processed to construct an image frame of the object. Typically, projection data is not weighted so that the frame rate may be increased. However, non-weighted projection data is known to produce noticeable shading and streaking in generated images. To reduce such shading and streaking, helical weighting algorithms may be used to weight the projection data corresponding to each frame. However, the more often projection data is filtered, weighted and backprojected, the slower the frame rate. The frame rate is thus limited to the computational capabilities of the CT Fluoro system.

It would be desirable, of course, to decrease computational redundancy in helical scan image reconstruction. It also would be desirable to facilitate altering the number of views per frame and offer reasonable trade-offs between views per frame and frame rate in CT fluoroscopic helical image reconstruction.

Solutions to the problems described above have not heretofore included significant remote capabilities. Thus, there is a need for a medical diagnostic system which provides for the advantages of remote services and addresses the problems above. For example, it would be desirable to provide remote services to such medical diagnostic systems. In particular, there is a need for remote upgrades, remote diagnostics, remote servicing, remote viewing, remote file storage, remote control, and remote adjustments to the segmentation algorithm or other system parameters and functions. Furthermore, remote services may provide for contractual arrangements, such as, per use licenses which lease the medical diagnostic equipment based on use. Additionally, remove services may also include expert on-line assistance for image scanning techniques, image analysis, pathology detection, imaging unit maintenance, and other expert-aided operations.

SUMMARY OF THE INVENTION

One embodiment of the invention relates to a method for producing a base tomographic image and a subsequent tomographic image of an object using projection data acquired in a scan with a system including an x-ray source and a detector array. The method includes applying a segmentation algorithm to the projection data to generate base image data comprising a plurality of segments; generating image data for each segment; generating subsequent image data based on said image data of each segment; and communicating image data, segments, subsequent image data, or base image data to a remote facility via a network. The remote facility provides remote services.

Other principle features and advantages of the present invention will become apparent to those skilled in the art upon review of the following drawings, the detailed description, and the appended claims.

BRIEF DESCRIPTION OF THE DRAWINGS

Preferred exemplary embodiments are described below with reference to the accompanying drawings, wherein like reference numerals denote like elements.

DETAILED DESCRIPTION OF THE PREFERRED EMBODIMENT

Figure 1:
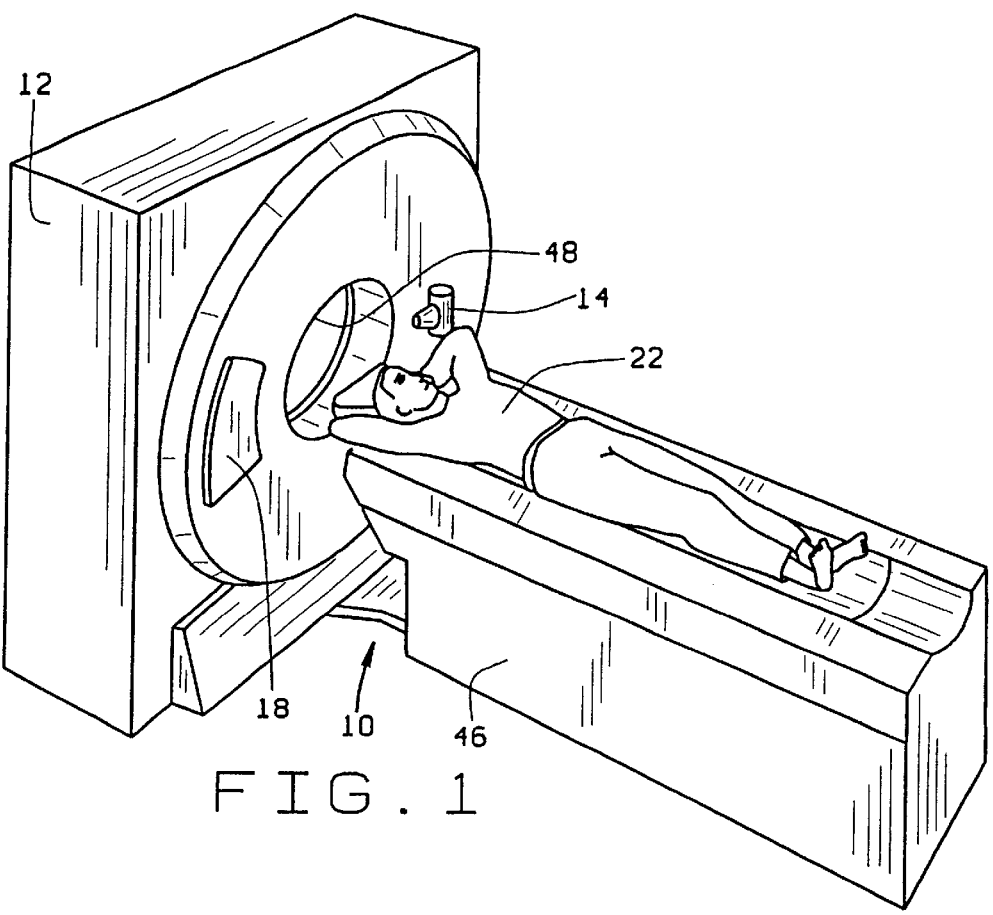
FIG. 1 is a pictorial view of a CT imaging system.
Figure 2:
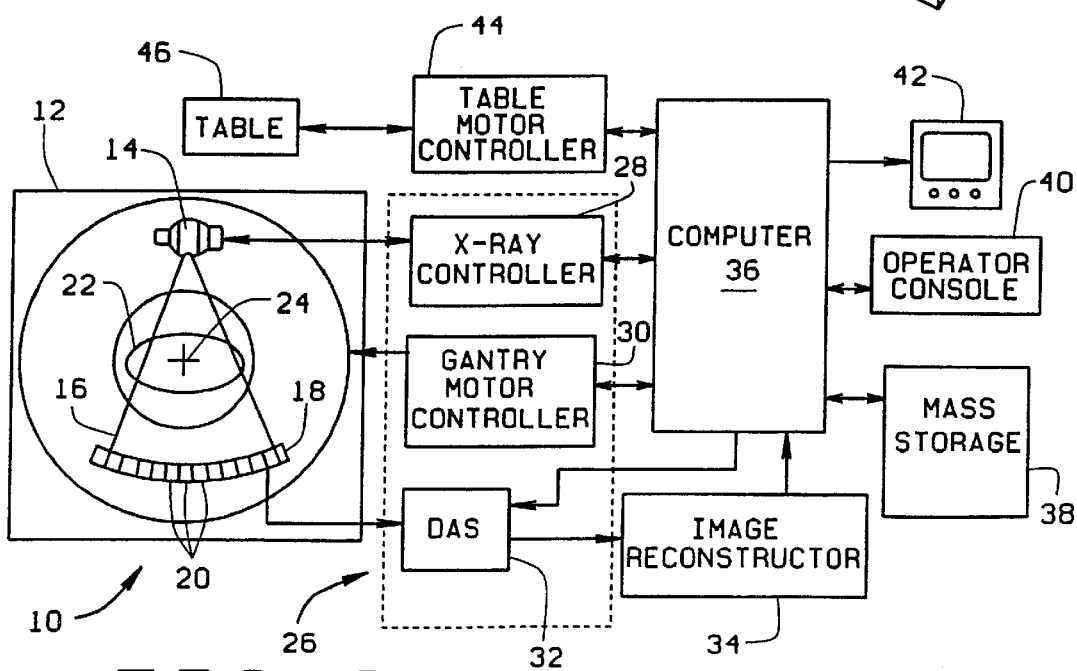
FIG. 2 is a block schematic diagram of the system illustrated in FIG. 1.

Referring to FIGS. 1 and 2, a computed tomograph (CT) imaging system 10 is shown as including a gantry 12 representative of a "third generation" CT scanner. Gantry 12 has an x-ray source 14 that projects a beam of x-rays 16 toward a detector array 18 on the opposite side of gantry 12. Detector array 18 is formed by detector elements 20 which together sense the projected x-rays that pass through a medical patient 22. Each detector element 20 produces an electrical signal that represents the intensity of an impinging x-ray beam and hence the attenuation of the beam as it passes through patient 22. During a scan to acquire x-ray projection data, gantry 12 and the components mounted thereon rotate about a center of rotation 24.

Rotation of gantry 12 and the operation of x-ray source 14 are governed by a control mechanism 26 of CT system 10. Control mechanism 26 includes an x-ray controller 28 that provides power and timing signals to x-ray source 14 and a gantry motor controller 30 that controls the rotational speed and position of gantry 12. A data acquisition system (DAS) 32 in control mechanism 26 samples analog data from detector elements 20 and converts the data to digital signals for subsequent processing. An image reconstructor 34 receives sampled and digitized x-ray data from DAS 32 and performs high speed image reconstruction. The reconstructed image is applied as an input to a computer 36 which stores the image in a mass storage device 38.

Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 which controls a motorized table 46 to position patient 22 in gantry 12. Particularly, table 46 moves portions of patient 22 through gantry opening 48.

The known helical reconstruction algorithms may generally be classified as Helical Extrapolative (HE) or Helical Interpolative (HI) algorithms. These algorithms typically apply a weighting factor to the projection data in order to reconstruct an image. This weighting factor is generally based on, i.e., dependent upon, both the fan angle and view angle. While the HE and HI algorithms provides generally acceptable image quality, such algorithms employ significant computational redundancies, and require significant hardware costs when reconstruction speed is crucial. For example, almost all projections that are used to generate an original image will have to be re-weighted, re-filtered, and re-backprojected to generate a new image that is even a small fraction of the rotation apart. Particularly, even where a significant amount of overlap occurs in projections of sequential images, to generate n images per gantry rotation, n times the amount of computation that is needed to generate a single image is needed during the gantry rotation.

The following discussion of a segmentation algorithm sometimes refers specifically to CT Fluoro systems using a helical scan or a cine scan. The segmentation algorithm, however, is not limited to practice in connection with such systems, and may be used with other CT systems. Further, in one embodiment, the segmentation algorithm would be implemented in computer 36 and would process, for example, data stored in mass storage 38. Many other alternative implementations are, of course, possible.

In accordance with one embodiment of the present invention, projection data to be used to generate base image data for a base image is divided into a plurality of segments.

Specifically, to generate the base image, gantry 12 rotates one full revolution plus a view angle of $\beta_0$, i.e., over the range $(0, 2\pi+\beta_0)$, to acquire projection data. Angle $\beta_0$ represents the angle of gantry rotation in excess of 360° during a helical scan, Views, V, represent the number of views collected per $2\pi$ gantry rotation, and views $V_L$ is the number of views contained in $(0 \leq \beta \leq \beta_0)$ view angle. The segmentation algorithm divides the projection data into M segments for every $2\pi$ angular span. For example, where system 10 speed is one second per gantry rotation and a data acquisition period of DAS 32 is five seconds, the projection data is divided into 5M segments. More specifically, the segmentation algorithm generates subsequent images from changed segments and allows selection of segment quantity and size from a variety of values, including segments having a different number of views from adjacent segments. Segment quantity and size are selected so that the number of views contained in the $k^{th}$ segment is identical to the $(k+M)^{th}$ segment and the quantity of views contained in any segment is greater than or equal to the number of views in $V_L$.

After dividing the projection data into segments and filtering the data, an overscan weighting algorithm is applied to the filtered projection data of each segment to generate overscan weight image data and unity image data for each segment, Specifically, the overscan weighting algorithm applies a weighting factor $w(\beta)$ to the projection data of each segment acquired at different view angles $ to generate an overscan weight image, $O_k$, for each segment. Note that for weighting purposes the starting view angle, $\beta$, for each segment is set to zero. A unity weighting factor is then applied to the projection data of each segment to generate a unity weight image, $U_k$, for each segment. Particularly, the filtered projection data is multiplied by the generated weighting factor, and then backprojected.

Utilizing segment image data from the base image data, subsequent image data is generated. More specifically and in one embodiment, the angular span for segment k is $\beta_k$ and the weights corresponding to regions $(0 \leq \beta \leq \beta_0)$ and $(2\pi \leq \beta \leq 2\pi+\beta_0)$ are complimentary to one another. Particularly, a view angle, $\beta_k$, for a first projection of a subsequent image is selected. Projection data contributing to the subsequent image is in the range $(\beta_k, 2\pi+\beta_k+\beta_0)$. By executing the segmentation algorithm, an updated weighting factor based on each view angle, $\beta_k$, and an overscan weighting factor $w(\beta)$ within the range $(0, 2\pi+\beta_0)$ is generated. Specifically, segmentation algorithm determines an updated weighting factor to apply to previously filtered, weighted, and backprojected base image projection data so that the subsequent image is generated without re-filtering, re-weighting and re-backprojecting all of the base image projection data.

FIG. 3a, for example, is a graph illustrating overscan weighting factors versus view angle for generating a first image in accordance with one embodiment of the present invention. FIG. 3b is a graph illustrating overscan weighting factors versus view angle for generating a subsequent image, wherein the subsequent image begins at view angle $\beta_k$. Particularly, $_k$ represents the view angle at which the first projection of the subsequent image is located, and the curve illustrates the weights applied to projection data for the generation of the subsequent image.

Figure 3:
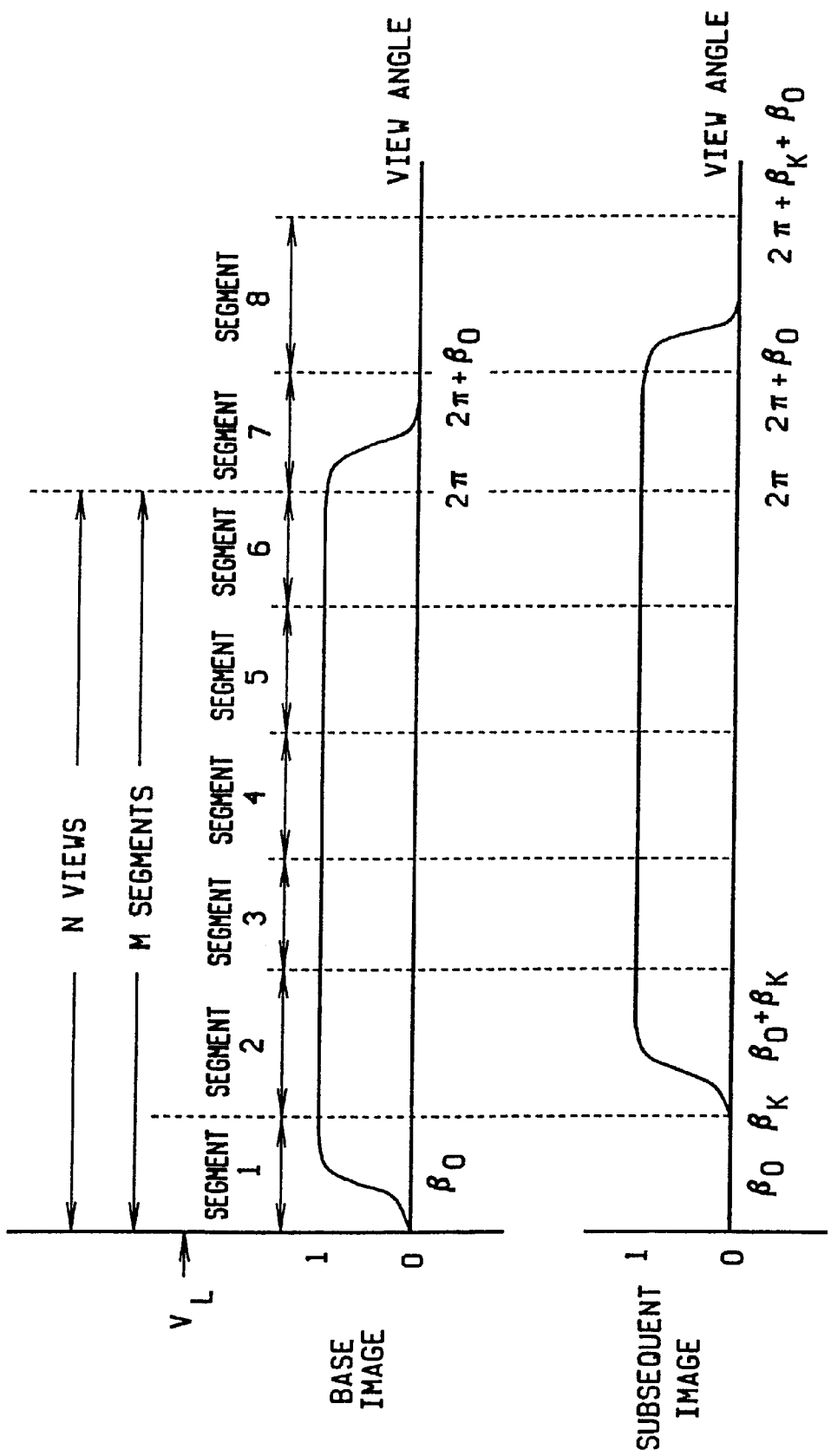
FIG. 3 is a graph illustrating overscan weighting factors versus view angle for generating a subsequent image from a base image in accordance with one embodiment of the present invention.

As shown in FIG. 3, the weighting factor for a majority of the segments remain unchanged between the base image and the $k^{th}$ subsequent image. For example and as shown in FIG. 3, the weighting factors of segments 3 through 6 are unchanged between the base image and the $k^{th}$ image. As a result, the $k^{th}$ image is:

$$P_k = O_k - O_{k+M} + \sum_{i=k+1}^{k+M} U_i$$

where:

$O_k$ is overscan weighted image data for segment k;

$U_i$ is unity weighted image data for segment i; and $k \leq 1$.

In addition, where M>6 and k>1, the $k^{th}$ image is:

$$P_k = P_k - 1 - O_k - 1 - U_k + O_k + O_{k+M-1} + U_{k+M} - O_{k+M}$$

where:

$O_k$ is overscan weighted image data for segment k;

$U_k$ is unity weighted image data for segment k;

k>1; and

M>6.

Therefore, the previously filtered, weighted and back-projected base image projection data is simply re-used to generate the subsequent image. Conversely, the overscan weighting factors applied to projection data in the segments 1 and 2, $(0, \beta_k+\beta_0)$, and segments 7 and 8, $(2\pi, 2\pi+\beta_k+\beta_0)$, differ between the first image and the subsequent image. The weighting algorithm thus generates weighting factors and image data within these ranges. More particularly, the weighting algorithm generates updated weighting factors which, when applied to the base image data, re-weights the base image data in the changed segments so that the base data contribution to the subsequent image is in accordance with the overscan weighting factors illustrated in FIG. 3b. However, such base image data is not re-filtered. Therefore, a substantial portion of the subsequent image is generated without re-filtering, re-weighting, or re-backprojecting the previously acquired base image data. Accordingly, significant amounts of filtering, multiplication, and back projection are eliminated, thus improving the computational efficiency of the system. More specifically, the only projection data required to be filtered to generate the subsequent image is projection data of segments previously not filtered for generating the base image data. As described above, this is not a substantial amount of data.

In one embodiment, the number of segments, M, is selected so that each segment contains an identical number of views, $v_k$. However, such a selection may be impractical. For example, the number of views contained in one gantry rotation, N, may not be divisible by the number of segments M. In addition, system 10 may include multiple processors, or processing pipes, D, used in parallel for image reconstruction, however, the number of views contained in each segment may not be divisible by the number of processors.

In another embodiment, a sampling rate of DAS 32 is adjusted so that the number of views after compression per $2\pi$ rotation, v, divided by the quantity of processor pipes D times the number of segment results in a whole integer. As shown in Table 1, illustrating an exemplary embodiment where DAS sampling rate is normally 984 views per rotation, the sampling rate of DAS 32 may be adjusted so that the selected number of views per segment are collected for a given image frame rate.

In an alternative embodiment, each segment includes multiple views and may be of a non-uniform size (different size from the neighboring segments). Specifically, the size of each segment may be altered so that the number of views in each segment divided by the number of pipes D is a whole number and the total number of views contained in the M segments is equal to the number of views per $2\pi$ rotation of gantry 12. In addition the segments must conform to the restrictions that the number of views contained in the $k^{th}$ segment is identical to the $(k+M)^{th}$ segment and the number of views in any segment must be greater than or equal to the $v_L$. An exemplary example is shown in Table 2.

In another embodiment, system 10 includes a convolution algorithm that simultaneously generates multiple views of a image data. Specifically, a complex FFT convolution algorithm simultaneously generates two views from the image data. More specifically, one view of N elements will be treated as the real part and the second view of N elements will be treated as the imaginary part of a complex sequence of length N. Particularly, a sequence y(n) is formed, sequence y(n) is:

$$y(n)=v_i(n)+jv_m(n)$$

where:
  n is the number of sample points and n=0, 1, 2, ..., N−1;
  i is the view number and i=0, 1, 2, ..., $N_{v-1}$;
  m is the view number and i=0, 1, 2, ..., $N_{v-1}$;
  $v_i$ corresponds to the $i^{th}$ zero padded view; and
  $v_m$ corresponds to the $m^{th}$ zero padded view.
  $v_i$ and $v_m$ may be from the same view, different views or different volumetric computed tomography slices.

After forming sequence y(n), a complex FFT of y(n), Y(n), is generated. An extended frequency domain response of the convolution kernel to N points is then generated where the response is:

H(k)=H(N−k)
  where k=N/2, ..., N−1; and
  H(k) is the real FFT of the kernel h(n), which is an even function.

Utilizing the extended frequency domain response H(k), Z(k) is computed:

$$Z(k)=Y(k)\cdot H(k).$$

An inverse complex FFT of Z(k), z(n) is generated and the result is separated, or isolated into Real z(n) and Imaginary z(n) portions or parts. Specifically, the portions are:
  $C_{vi}$=Real z(n);
  $C_{vm}$=Imaginary z(n),
where:
  $C_{vi}$ is the convolved $i^{th}$ view; and
  $C_{vm}$ is the $m^{th}$ view.

Utilizing the convolution algorithm reduces the numbers of forward and reverse complex FFT operations that must be performed. For example, where four views are processed, known convolution algorithms must perform four forward and four inverse Real FFT operations. However, the convolution algorithm described generates the image data by requiring only two forward and two inverse complex FFT operations. As a result, the computational efficiency is improved and the amount of time required to generate the images may be reduced.

The above described algorithm facilitates improving computational efficiency without degrading image quality in CT Fluoro image reconstruction. Such algorithm also decreases the processing time and offers reasonable trade-offs between number of views and frame rate.

From the preceding description of various embodiments of the present invention, it is evident that the objects of the invention are attained. Although the invention has been described and illustrated in detail, it is to be clearly understood that the same is intended by way of illustration and example only and is not to be taken by way of limitation. For example, the CT system described herein is a CT Fluoro system. Many other CT systems may be used. Similarly, while the values of $\beta$ and $\beta_k$ are described herein as being selected as the final stage of image quality evaluation, any or all of these values may be pre-selected and stored in the computer. Furthermore, the overscan weights described are determined in accordance to a non-linear function, i.e., w($\beta$) is not proportional to $\beta$. However, the overscan weights may be generated with a linear function, or with a different non-linear function. In addition, while the invention is described in connection with a helical scan, the invention may also be used in connection with a cine scan. Accordingly, the spirit and scope of the invention are to be limited only by the terms of the appended claims.

Figure 4:
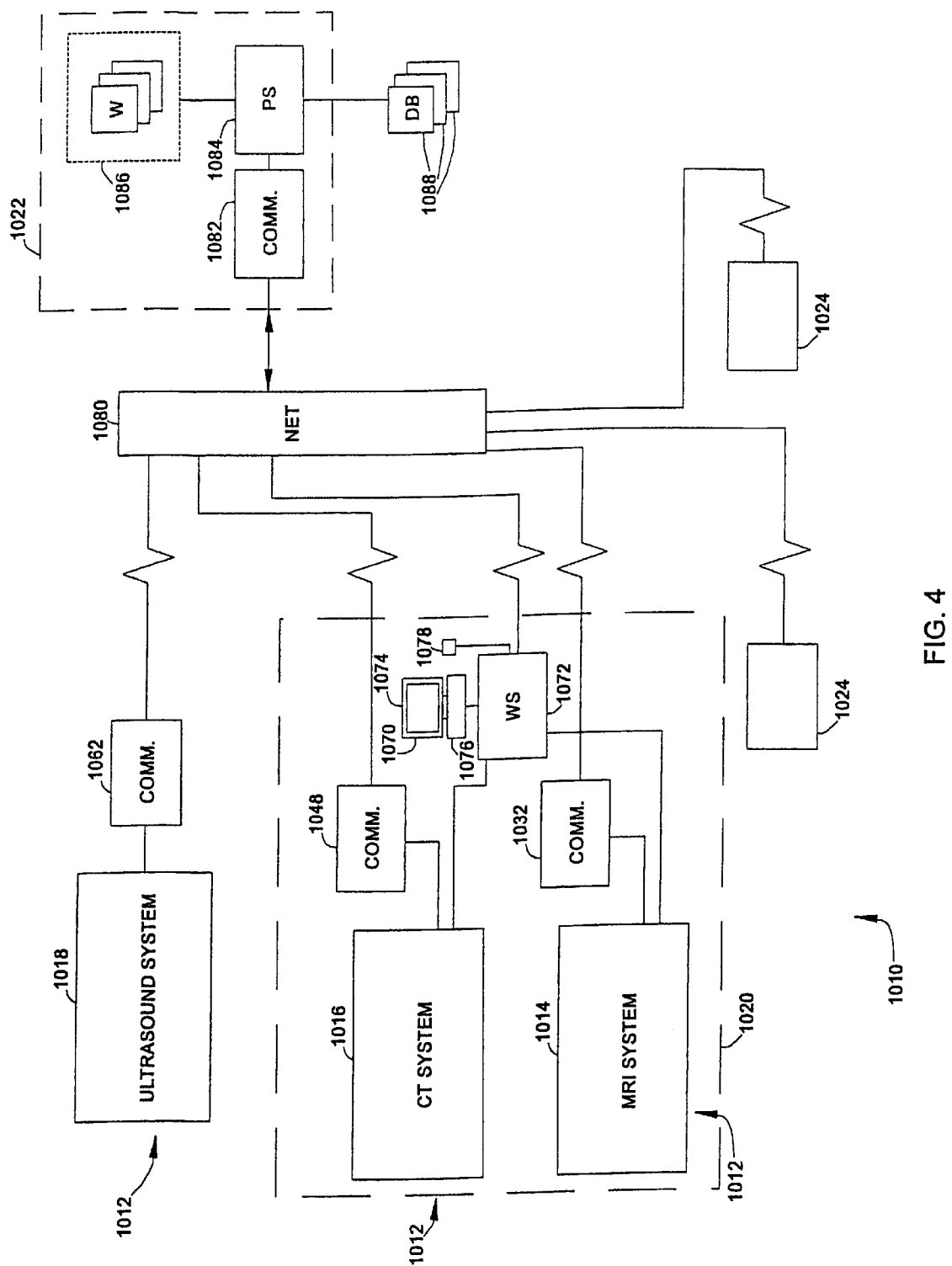
FIG. 4 is a diagrammatical representation of a series of medical diagnostic systems coupled to a service facility via a network connection for providing remote services and data interchange between the diagnostic systems and the service facility.

Referring now to FIG. 4, a service system 1010 is illustrated for providing remote service to a plurality of medical diagnostic systems 1012, including systems such as CT imaging system 10 described with reference to FIG. 1. In the embodiment illustrated in FIG. 4, the medical diagnostic systems include a magnetic resonance imaging (MRI) system 1014, a computed tomography (CT) system 1016, and an ultrasound imaging system 1018. The diagnostic systems may be positioned in a single location or facility, such as a medical facility 1020, or may be remote from one another as shown in the case of ultrasound system 1018. The diagnostic systems are serviced from a centralized service facility 1022. Moreover, a plurality of field service units 1024 may be coupled in the service system for transmitting service requests, verifying service status, transmitting service data and so forth as described more fully below.

In the exemplary embodiment of FIG. 4, several different system modalities are provided with remote service by the service facility. Remote services include but are not limited to services, such as, remote monitoring, remote system control, imediate file access from remote locations, remote file storage and archiving, remote resource pooling, remote recording, and remote high speed computations. Remote services are provided to a particular modality depending upon the capabilities of the service facility, the types of diagnostic systems subscribing to service contracts with the facility, as well as other factors.

Depending upon the modality of the systems, various subcomponents or subsystems will be included. In the case of MRI system 1014, such systems will generally include a scanner, a control and signal detection circuit, a system controller, and an operator station. MRI system 1014 includes a uniform platform for interactively exchanging service requests, messages and data with service facility 1022 as described more fully below. MRI system 1014 is linked to a communications module 1032, which may be included in a single or separate physical package from MRI system 1014. In a typical system, additional components may be included in system 1014, such as a printer or photographic system for producing reconstructed images based upon data collected from the scanner.

Similarly, CT system 1016 will typically include a scanner, a signal acquisition unit, and a system controller. The scanner detects portions of x-ray radiation directed through a subject of interest. The controller includes circuitry for commanding operation of the scanner and for processing and reconstructing image data based upon the acquired signals. CT system 1016 is linked to a communications module 1048 for transmitting and receiving data for remote services. Moreover, like MRI system 1014, CT system 1016 will generally include a printer or similar device for outputting reconstructed imnages based upon data collected by the scanner.

In the case of ultrasound system 1018, such systems will generally include a scanner and data processing unit and a system controller. Ultrasound system 1018 is coupled to a communications module 1062 for transmitting service requests, messages and data between ultrasound system 1018 and service facility 1022.

Although reference is made herein generally to "scanners" in diagnostic systems, that term should be understood to include medical diagnostic data acquisition equipment generally, not limited to image data acquisition, as well as to picture archiving communications and retrieval systems, image management systems, facility or institution management systems, viewing systems and the like, in the field of medical diagnostics.

Where more than one medical diagnostic system is provided in a single facility or location, as indicated in the case of MRI and CT systems 1014 and 1016 in FIG. 4, these may be coupled to a management station 1070, such as in a radiology department of a hospital or clinic. The management station may be linked directly to controllers for the various diagnostic systems. The management system may include a computer workstation or personal computer 1072 coupled to the system controllers in an intranet configuration, in a file sharing configuration, a client/server arrangement, or in any other suitable manner. Moreover, management station 1070 will typically include a monitor 1074 for viewing system operational parameters, analyzing system utilization, and exchanging service requests and data between the facility 1020 and the service facility 1022. Input devices, such as a standard computer keyboard 1076 and mouse 1078, may also be provided to facilitate the user interface.

It should be noted that, alternatively, the management system, or other diagnostic system components, may be "stand-alone" or not coupled directly to a diagnostic system. In such cases, the service platform described herein, and some or all of the service functionality nevertheless be provided on the management system. Similarly, in certain applications, a diagnostic system may consist of a standalone or networked picture archiving communications and retrieval system or a viewing station provided with some or all of the functionality described herein.

The communication modules mentioned above, as well as workstation 1072 and field service units 1024 may be linked to service facility 1022 via a remote access network 1080. For this purpose, any suitable network connection may be employed. Presently preferred network configurations include both proprietary or dedicated networks, as well as open networks, such as the Internet. Data may be exchanged between the diagnostic systems, field service units, and remote service facility 1022 in any suitable format, such as in accordance with the Internet Protocol (IP), the Transmission Control Protocol (TCP), or other known protocols. Moreover, certain of the data may be transmitted or formatted via markup languages such as the HyperText Markup Language (HTML), or other standard languages. The presently preferred interface structures and communications components are described in greater detail below.

Within service facility 1022, messages, service requests and data are received by communication components as indicated generally at reference numeral 1082. Components 1082 transmit the service data to a service center processing system, represented generally at reference numeral 1084 in FIG. 4. The processing system manages the receipt, handling and transmission of service data to and from the service facility. In general, processing system 1084 may include one or a plurality of computers, as well as dedicated hardware or software servers for processing the various service requests and for receiving and transmitting the service data as described more fully below.

Service facility 1022 also includes a bank of operator workstations 1086 which may be staffed by personnel who address the service requests and provide off and on-line service to the diagnostic systems in response to the service requests. Also, processing system 1084 may be linked to a system of databases or other processing systems 1088 at or remote from the service facility 1022. Such databases and processing systems may include extensive database information on operating parameters, service histories, and so forth, both for particular subscribing scanners, as well as for extended populations of diagnostic equipment.

Figure 5:
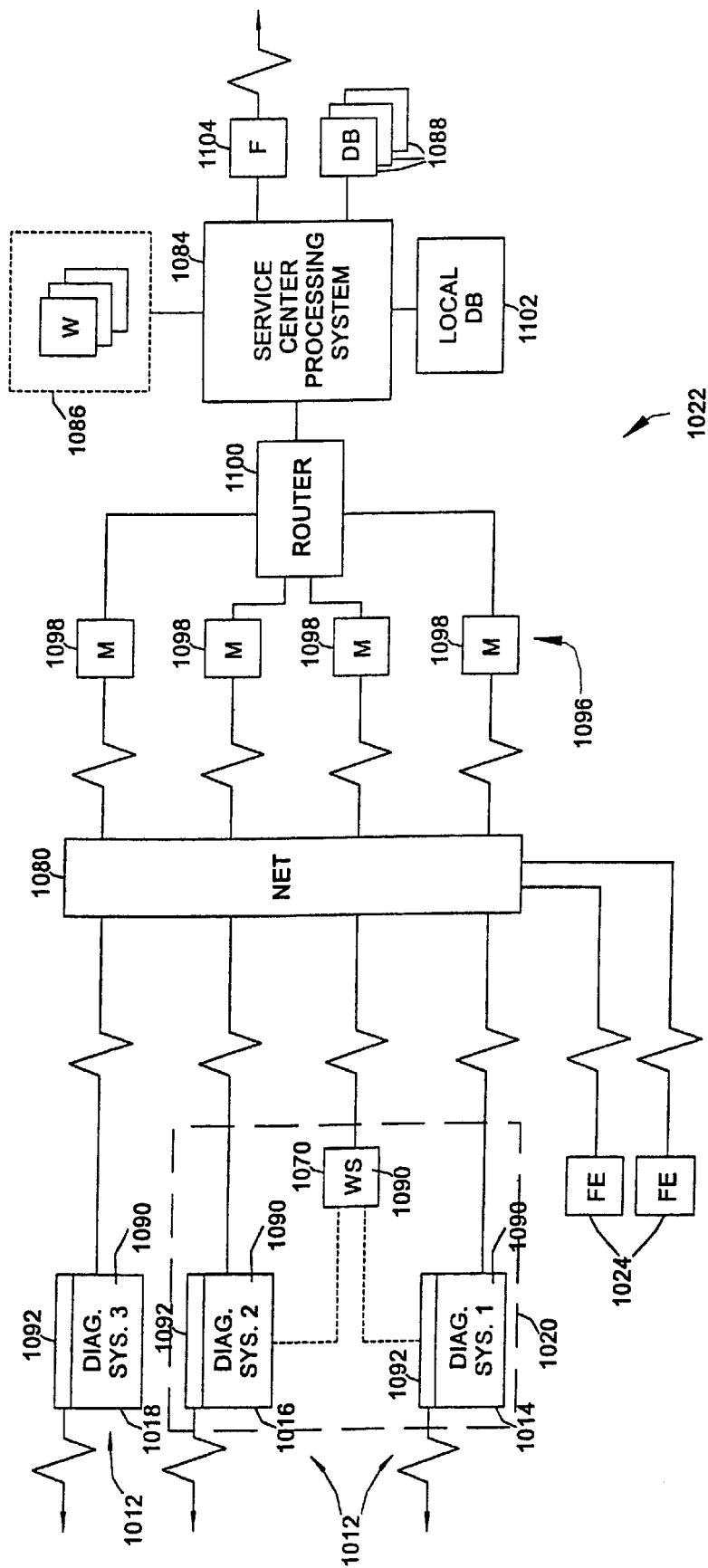
FIG. 5 is a block diagram of the systems shown in FIG. 4 illustrating certain functional components of the diagnostic systems and the service facility.

FIG. 5 is a block diagram illustrating the foregoing system components in a functional view. As shown in FIG. 5, the field service units 1024 and the diagnostic systems 1012 can be linked to the service facility 1022 via a network connection as illustrated generally at reference numeral 1080. Within each diagnostic system 1012, a uniform service platform 1090 is provided.

Platform 1090, which is described in greater detail below with particular reference to FIG. 6, includes hardware, firmware, and software components adapted for composing service requests, transmitting and receiving service data, establishing network connections and managing financial or subscriber arrangements between diagnostic systems and the service facility. Moreover, the platforms provide a uniform graphical user interface at each diagnostic system, which can be adapted to various system modalities to facilitate interaction of clinicians and radiologists with the various diagnostic systems for service functions. The platforms enable the scanner designer to interface directly with the control circuitry of the individual scanners, as well as with memory devices at the scanners, to access image, log and similar files needed for rendering requested or subscribed services. Where a management station 1070 is provided, a similar uniform platform is preferably loaded on the management station to facilitate direct interfacing between the management station and the service facility. In addition to the uniform service platform 1090, each diagnostic system is preferably provided with an alternative communications module 1092, such as a facsimile transmission module for sending and receiving facsimile messages between the scanner and remote service facilities.

Messages and data transmitted between the diagnostic systems and the service facility traverse a security barrier or "firewall" contained within processing system 1084 as discussed below, which prevents unauthorized access to the service facility in a manner generally known in the art. A modem rack 1096, including a series of modems 1098, receives the incoming data, and transmits outgoing data through a router 1100 which manages data traffic between the modems and the service center processing system 1084.

In the diagram of FIG. 5, operator workstations 1086 are coupled to the processing system, as are remote databases or computers 1088. In addition, at least one local service database 1102 is provided for verifying license and contract arrangements, storing service record files, log files, and so forth. Moreover, one or more communication modules 1104 are linked to processing system 1084 to send and receive facsimile transmissions between the service facility and the diagnostic systems or field service units.

Figure 6:
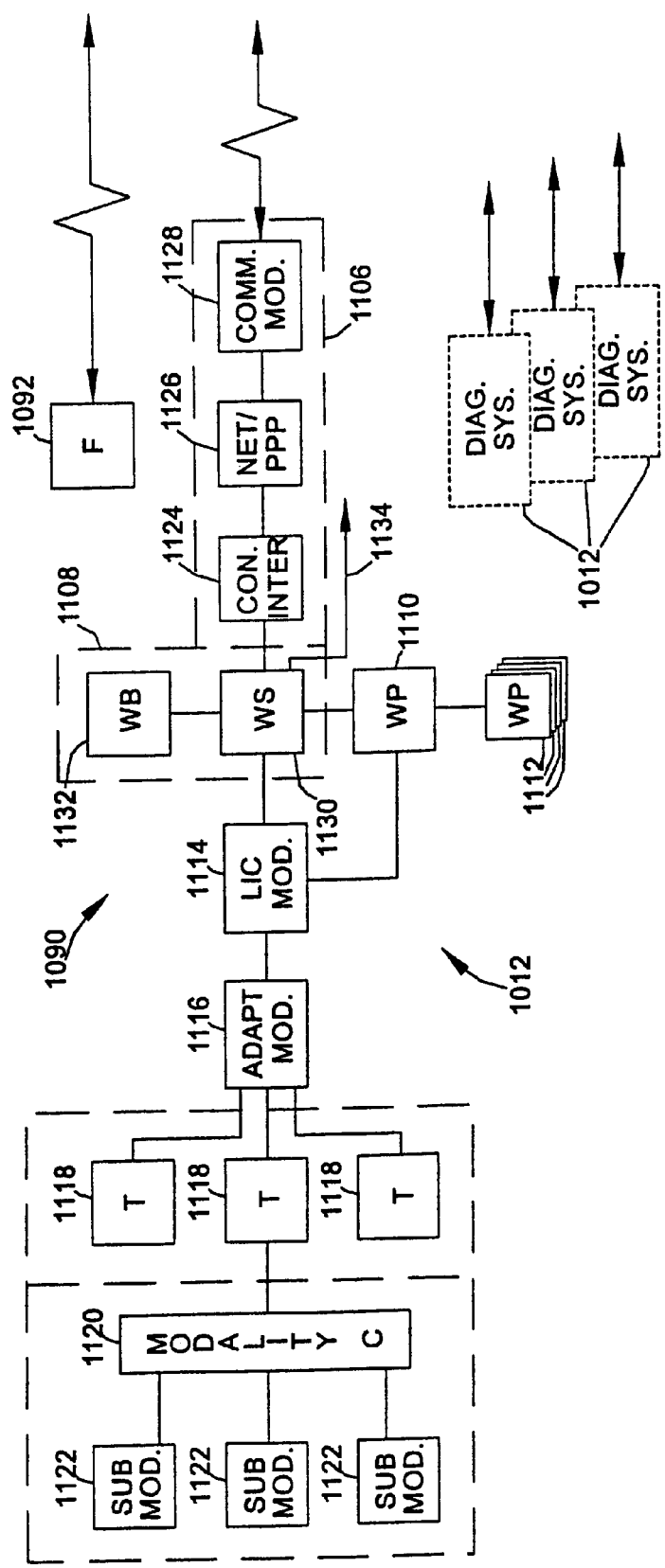
FIG. 6 is a block diagram of certain functional components within a diagnostic system of the type shown in FIG. 4 and FIG. 5 for facilitating interactive remote servicing of the diagnostic system.

FIG. 6 illustrates diagrammatically the various functional components comprising the uniform service platform 1090 within each diagnostic system 1012. As shown in FIG. 6, the uniform platform includes a device connectivity module 1106, as well as a network connectivity module 1108. Network connectivity module 1108 accesses a main web page 1110 which, as mentioned above, is preferably a markup language page, such as an HTML page displayed for the system user on a monitor at the diagnostic system. Main web page 1110 is preferably accessible from a normal operating page in which the user will configure examination requests, view the results of examinations, and so forth such as via an on-screen icon. Through main web page 1110, a series of additional web pages 1112 are accessible. Such web pages permit remote service requests to be composed and transmitted to the remote service facility, and facilitate the exchange of other messages, reports, software, protocols, and so forth as described more fully below.

It should be noted that as used herein the term "page" includes a user interface screen or similar arrangement which can be viewed by a user of the diagnostic system, such as screens providing graphical or textual representations of data, messages, reports and so forth. Moreover, such pages may be defined by a markup language or a programming language such as Java, perl, java script, or any other suitable language.

Network connectivity module 1108 is coupled to a license module 1114 for verifying the status of license, fee or contractual subscriptions between the diagnostic system and the service facility. As used herein, the term "subscription" should be understood to include various arrangements, contractual, commercial or otherwise for the provision of services, information, software, and the like, both accompanies with or without payment of a fee. Moreover, the particular arrangements manages by systems as described below may include several different types of subscriptions, including time-expiring arrangements, one-time fee arrangements, and so-called "pay per use" arrangements, to mention but a few.

License module 1114 is, in turn, coupled to one or more adapter utilities 1116 for interfacing the browser, server, and communications components with modality interface tools 1118. In a presently preferred configuration, several such interface tools are provided for exchanging data between the system scanner and the service platform. For example, modality interface tools 1118 may include applets or servlets for building modality-specific applications, as well as configuration templates, graphical user interface customization code, and so forth. Adapters 1116 may interact with such components, or directly with a modality controller 1120 which is coupled to modality-specific subcomponents 1122.

The modality controller 1120 and modality-specific subcomponents 1122 will typically include a preconfigured processor or computer for executing examinations, and memory circuitry for storing image data files, log files, error files, and so forth. Adapter 1116 may interface with such circuitry to convert the stored data to and from desired protocols, such as between the HyperText Transfer Protocol (HTTP) and DICOM, a medical imaging standard for data presentation. Moreover, transfer of files and data as described below may be performed via any suitable protocol, such as a file transfer protocol (FTP) or other network protocol.

In the illustrated embodiment, device connectivity module 1106 includes several components for providing data exchange between the diagnostic system and the remote service facility. In particular, a connectivity service module 1124 provides for interfacing with network connectivity module 1108. A Point-to-Point Protocol (PPP) module 1126 is also provided for transmitting Internet Protocol (IP) packets over remote communication corrections. Finally, a modem 1128 is provided for receiving and transmitting data between the diagnostic system and the remote service facility. As will be appreciated by those skilled in the art, various other network protocols and components may be employed within device connectivity module 1106 for facilitating such data exchange.

Network connectivity module 1108 preferably includes a server 1130 and a browser 1132. Server 1130 facilitates data exchange between the diagnostic system and the service facility, and permits a series of web pages 1110 and 1112 to be viewed via browser 1132. In a presently preferred embodiment, server 1130 and browser 1132 support HTTP applications and the browser supports java applications. Other servers and browsers, or similar software packages may, of course, be employed for exchanging data, service requests, messages, and software between the diagnostic system, the operator and the remote service facility. Finally, a direct network connection 1134 may be provided between server 1130 and an operator workstation, such as management station 1070 within the medical facility (see FIGS. 4 and 5).

In a present embodiment, the components comprising network connectivity module may be configured via an application stored as part of the uniform platform. In particular, a Java application licensed to a service engineer enables the engineer to configure the device connectivity at the diagnostic system to permit it to connect with the service facility.

Figure 7:
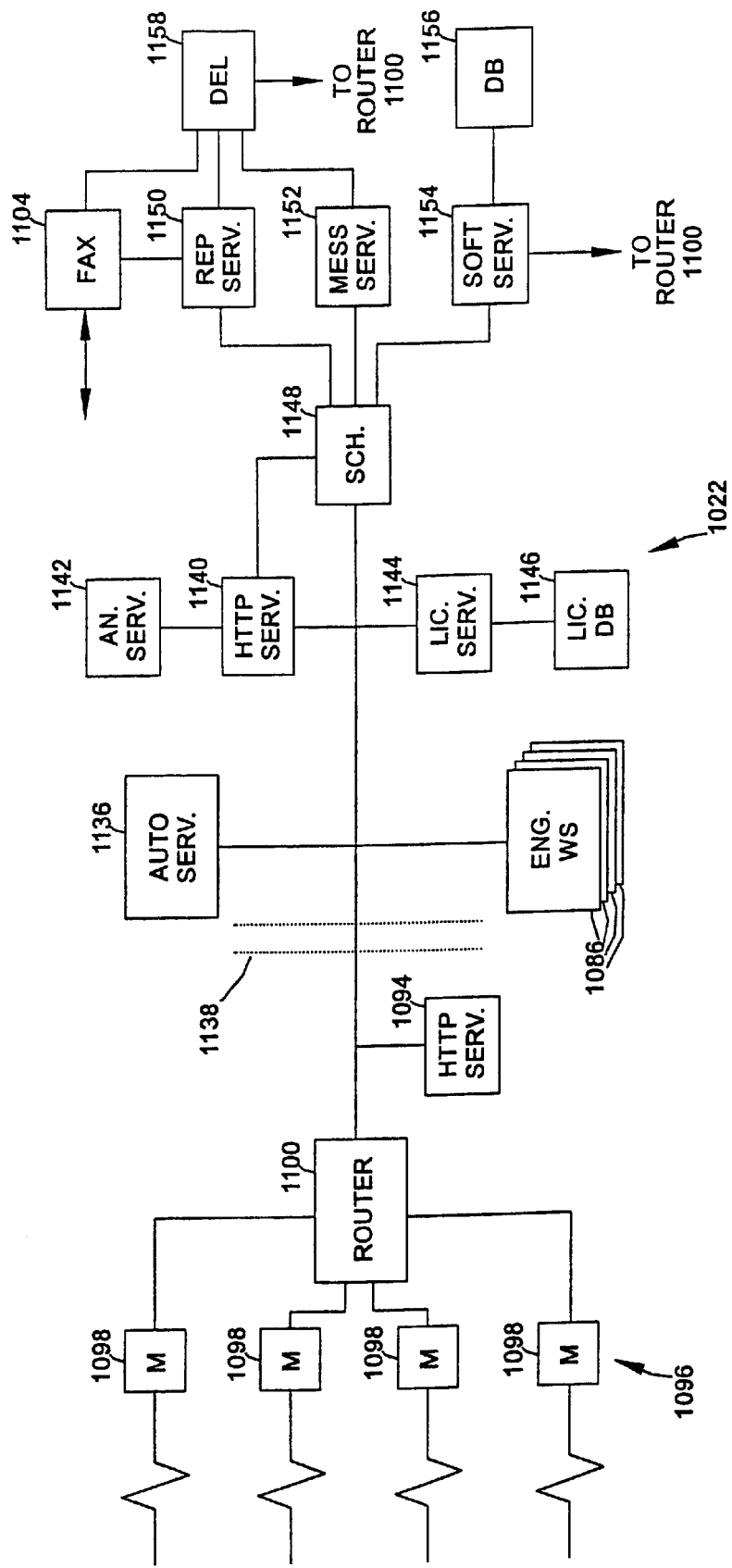
FIG. 7 is a block diagram of certain of the functional components of the service facility illustrated in FIG. 4 and FIG. 5 for rendering interactive remote service to a plurality of medical diagnostic systems.

FIG. 7 illustrates exemplary functional components for service facility 1022. As indicated above, service facility 1022 includes a modem rack 1096 comprising a plurality of modems 1098 coupled to a router 1100 for coordinating data communications with the service facility. An HTTP service server 1094 receives and directs incoming and outgoing transactions with the facility. Server 1094 is coupled to the other components of the facility through a firewall 1138 for system security. Operator workstations 1086 are coupled to the port manager for handling service requests and transmitting messages and reports in response to such requests.

An automated service unit 1136 may also be included in the service facility for automatically responding to certain service requests, sweeping subscribing diagnostic systems for operational parameter data, and so forth, as described below. In a presently preferred embodiment, the automated service unit may operate independently of or in conjunction with the interactive service components comprising processing system 1084. It should be noted that other network or communications schemes may be provided for enabling the service facility to communicate and exchange data and messages with diagnostic systems and remote service units, such as systems including outside Internet service providers (ISP's), virtual private networks (VPN's) and so forth.

Behind firewall 1138, an HTTP application server 1140 coordinates handling of service requests, messaging, reporting, software transfers and so forth. Other servers may be coupled to HTTP server 1140, such as service analysis servers 1142 configured to address specific types of service requests, as described more fully below. In the illustrated embodiment, processing system 1084 also includes a license server 1144 which is coupled to a license database 1146 for storing, updating and verifying the status of diagnostic system service subscriptions. Alternatively, where desired, license server 1144 may be placed outside of fire wall 1138 to verify subscription status prior to admission to the service facility.

Handling of service requests, messaging, and reporting is further coordinated by a scheduler module 1148 coupled to RTTP server 1140. Scheduler module 1148 coordinates activities of other servers comprising the processing system, such as a report server 1150, a message server 1152, and a software download server 1154. As will be appreciated by those skilled in the art, servers 1150, 1152 and 1154 are coupled to memory devices (not shown) for storing data such as addresses, log files, message and report files, applications software, and so forth. In particular, as illustrated in FIG. 7, software server 1154 is coupled via one or more data channels to a storage device 1156 for containing transmittable software packages which may be sent directly to the diagnostic systems, accessed by the diagnostic systems, or supplied on pay-per-use or purchase basis. Message and report servers 1152 and 1150 are further coupled, along with communications module 1104, to a delivery handling module 1158, which is configured to receive outgoing messages, insure proper connectivity with diagnostic systems, and coordinate transmission of the messages.

In a presently preferred embodiment, the foregoing functional circuitry may be configured as hardware, firmware, or software on any appropriate computer platform. For example, the functional circuitry of the diagnostic systems may be programmed as appropriate code in a personnel computer or workstation either incorporated entirely in or added to the system scanner. The functional circuitry of the service facility may include additional personal computers or workstations, in addition to a main frame computer in which one or more of the servers, the scheduler, and so forth, are configured. Finally, the field service units may comprise personal computers or laptop computers of any suitable processor platform. It should also be noted that the foregoing functional circuitry may be adapted in a variety of manners for executing the functions described herein. In general, the functional circuitry facilitates the exchange of remote service data between the diagnostic systems and a remote service facility, which is preferably implemented in an interactive manner to provide regular updates to the diagnostic systems of service activities.

As described above, both the diagnostic systems and the field service units preferably facilitate interfacing between a variety of diagnostic system modalities and the remote service facility via a series of interactive user-viewable pages. Exemplary pages include capabilities of providing interactive information, composing service requests, selecting and transferring messages, reports and diagnostic system software, and so forth. Pages facilitate the interaction and use of remote services, such as, remote monitoring, remote system control, immediate file access from remote locations, remote file storage and archiving, remote resource pooling, remote recording, and remote high speed computations.

The user can access specific documents described in text areas of the pages by selection of all or a portion of the text describing the documents. In the presently preferred embodiment, the accessed documents may be stored in local memory devices within the diagnostic system, or selection of the text may result in loading of a uniform resource locator (URL) for accessing a remote computer or server via a network link.

Advantageously, service system 1010 (FIG. 4) provides the remote services, such as, remote upgrades, remote diagnostics, remote servicing, remote viewing, remote file storage, remote control, and remote adjustments to the segmentation algorithm or other system parameters and functions. Furthermore, remote services may provide for contractual arrangements, such as, per use licenses which lease the medical diagnostic equipment based on use. Additionally, remote services may also include expert on-line assistance for image scanning techniques, image analysis, pathology detection, imaging unit maintenance, and other expert-aided operations.

While the embodiments illustrated in the Figures and described above are presently preferred, it should be understood that the embodiments are offered by way of example only. Other embodiments may include enhanced remote features made possible by the network structures and functionalities described herein. The invention is not limited to a particular embodiment, but extends to various modifications, combinations, and permutations that nevertheless fall within the scope and spirit of the appended claims.

What is claimed is:

1. A method for producing a base tomographic image and a subsequent tomographic image of an object using projection data acquired in a scan with a system comprising an x-ray source and a detector array, the detector array, the method comprising:

applying a segmentation algorithm to the projection data to generate base image data comprising a plurality of segments;

generating image data for each segment;

generating subsequent image data based on the image data of each segment; and communicating image data, segments, subsequent image data, or base image data to a remote facility via a network, the remote facility providing remote services.

2. A method in accordance with claim 1 wherein generating the image data for each segment comprises generating overscan weighted image data and unity weighted image data for each segment.

3. A method in accordance with claim 2 wherein generating the base image data comprises dividing the base image data into M segments for every $2\pi$ angular span.

4. A method in accordance with claim 3 wherein the subsequent image data P of segment k is:

$$P_k = O_k - O_{k+M} + \sum_{i=k+1}^{k+M} U_i$$

where:

$O_k$ is overscan weighted image data for segment k;

$U_i$ is unity weighted image data for segment i; and $k \leq 1$.

5. A method in accordance with claim 3 wherein the subsequent image data P of segment k is:

$$P_k = P_k - 1 - O_k - 1 - U_k + O_k + O_{k+M-1} + U_{k+M} - O_{k+M}$$

where:

$O_k$ is overscan weighted image data for segment k;

$U_k$ is unity weighted image data for segment k;

k>1; and

M>6.

6. A method in accordance with claim 3 wherein each segment comprises multiple number of views.

7. A method in accordance with claim 6 wherein the number of views in $k^{th}$ segment equals the number of views in $(k+M)^{th}$ segment.

8. A method in accordance with claim 7 further comprising a number of processor pipes D and wherein the number of views in each segment is greater than or equal to the number of views in $0 \leq \beta \leq \beta_0$, where:

β is a view angle; and $\beta_0$ is an angle of gantry rotation in excess of 360° for image reconstruction.

9. A method in accordance with claim 8 further comprising a data acquisition system (DAS) and wherein to select the number of views per segment, the system is configured to adjust a DAS data sampling rate so that the selected number of views per segment are collected.

10. A method in accordance with claim 9 wherein the adjusted sampling rate is:

$$R = V/(D*M),$$

where:

R is a whole integer number; and

V is a number of views per 2π rotation of gantry.

11. A method in accordance with claim 8 wherein the selected number of views in each processor pipe is:

$v_k$=(number of views in segment k)/D where:

$v_k$ is a whole integer.

12. A method in accordance with claim 2 further comprising a convolution algorithm to simultaneously generate two views of image data.

13. A method in accordance with claim 12 wherein the convolution algorithm is configured to:

form a sequence y(n);

determine Y(k); and determine an extended frequency domain response to N−1 points, where:

$y(n)=v_i(n)+jv_m(n)$;

Y(k) is a complex FFT of y(n);

n is a number of sample points ranging from 0 to N−1;

i is a view number ranging from 0 to $N_{v-1}$;

m is a view number ranging from 0 to $N_{v-1}$;

$v_i$ corresponds to the $i^{th}$ zero padded view; and $v_m$ corresponds to the $m^{th}$ zero padded view.

14. A method in accordance with claim 13 wherein i is not equal to m.

15. A method in accordance with claim 13 wherein $v_i$ and $v_m$ correspond to different slices of a volumetric scan.

16. A method in accordance with claim 13 wherein the extended frequency domain response is:

H(k)=H(N−k), where:

k=N/2 . . . N−1; and spatial response of a h(n) kernel is an even function.

17. A method in accordance with claim 13 wherein the convolution algorithm is further configured to:

determine a Z(k);

determine a inverse complex FFT, z(k), of Z(k); and isolate real part $Cv_i$ and imaginary part $Cv_m$ of z(n);

where: Z(k)=Y(k)·H(k).

* * * * *

UNITED STATES PATENT AND TRADEMARK OFFICE
CERTIFICATE OF CORRECTION

PATENT NO. : 6,298,112 B1
DATED : October 2, 2001
INVENTOR(S) : Acharya et al.

It is certified that error appears in the above-identified patent and that said Letters Patent is hereby corrected as shown below:

<u>Title page</u>,
Item [75], "Waukesha" to -- Brookfield --.

<u>Column 1</u>,
Line 13, delete "Achar a" and replace with -- Acharya --.

<u>Column 5</u>,
Line 25, after "segment," delete "," and insert -- . --.

<u>Column 9</u>,
Line 2, delete "imnages" and replace with -- images --.

<u>Column 11</u>,
Line 32, delete "panies" and replace with -- panied --.
Line 33, delete "manages" and replace with -- managed --.

<u>Column 12</u>,
Line 65, delete "fire wall" and replace with -- firewall --.

<u>Column 13</u>,
Line 3, delete "RTTP" and replace with -- HTTP --.

Signed and Sealed this

Twenty-third Day of July, 2002

*Attest:*

*Attesting Officer*

JAMES E. ROGAN
*Director of the United States Patent and Trademark Office*